United States Patent
Levy

(10) Patent No.: US 8,632,467 B2
(45) Date of Patent: Jan. 21, 2014

(54) ROTATIONAL SHAPE-MEMORY ACTUATORS AND ASSOCIATED DEVICES, SYSTEMS, AND METHODS

(71) Applicant: Volcano Corporation, San Diego, CA (US)

(72) Inventor: Oren Levy, Emerald Hills, CA (US)

(73) Assignee: Volcano Corporation, San Diego, CA (US)

(*) Notice: Subject to any disclaimer, the term of this patent is extended or adjusted under 35 U.S.C. 154(b) by 0 days.

(21) Appl. No.: 13/649,894

(22) Filed: Oct. 11, 2012

(65) Prior Publication Data
US 2013/0096426 A1  Apr. 18, 2013

Related U.S. Application Data

(60) Provisional application No. 61/546,419, filed on Oct. 12, 2011, provisional application No. 61/579,984, filed on Dec. 23, 2011.

(51) Int. Cl.
*A61B 8/14* (2006.01)

(52) U.S. Cl.
USPC ........... 600/459; 600/462; 600/466; 600/139; 600/143

(58) Field of Classification Search
USPC .................. 600/407–480, 139–144
See application file for complete search history.

(56) References Cited

U.S. PATENT DOCUMENTS

| | | | |
|---|---|---|---|
| 4,106,492 A | 8/1978 | Schuette et al. | |
| 4,794,931 A | 1/1989 | Yock | |
| 4,841,977 A | 6/1989 | Griffith et al. | |
| 4,887,605 A | 12/1989 | Angelsen et al. | |
| 5,000,185 A | 3/1991 | Yock | |
| 5,181,514 A | 1/1993 | Solomon et al. | |
| 5,203,337 A | 4/1993 | Feldman | |
| 5,238,005 A | 8/1993 | Imran | |
| 5,271,402 A | 12/1993 | Yeung | |
| 5,349,964 A | 9/1994 | Imran | |

(Continued)

FOREIGN PATENT DOCUMENTS

| | | |
|---|---|---|
| DE | 4238176 A1 | 5/1994 |
| WO | WO 97/23865 A | 7/1997 |

(Continued)

OTHER PUBLICATIONS

International Search Report and Written Opinion issued on Aug. 28, 2006 for PCT/US2006/016599.

(Continued)

*Primary Examiner* — Sanjay Cattungal
(74) *Attorney, Agent, or Firm* — Haynes and Boone, LLP

(57) ABSTRACT

Rotational shape-memory actuators and associated devices, systems, and methods are disclosed. In some embodiments, a rotational shape-memory actuator includes a first anchor, a second anchor, a spring element extending between the first and second anchors, a first shape memory element extending between the first and second anchors, a second shape memory element extending between the first and second anchors, and a communication line wrapped around the first and second shape memory elements. The first and second shape memory elements are configured to transition between a first configuration in which the first and second shape memory elements are twisted together and a second configuration in which the first and second shape memory elements are less twisted together such that transitions of the first and second shape memory elements between the first and second configurations cause the second anchor to rotate with respect to the first anchor.

29 Claims, 15 Drawing Sheets

(56) References Cited

U.S. PATENT DOCUMENTS

| | | | |
|---|---|---|---|
| 5,373,845 A | 12/1994 | Gardineer et al. |
| 5,373,849 A | 12/1994 | Maroney et al. |
| 5,377,685 A | 1/1995 | Kazi et al. |
| 5,379,772 A | 1/1995 | Imran |
| 5,383,923 A | 1/1995 | Webster, Jr. |
| 5,409,000 A | 4/1995 | Imran |
| 5,409,453 A | 4/1995 | Lundquist et al. |
| 5,467,779 A | 11/1995 | Smith et al. |
| 5,478,330 A | 12/1995 | Imran et al. |
| 5,482,029 A | 1/1996 | Sekiguchi et al. |
| 5,549,542 A | 8/1996 | Kovalcheck |
| 5,606,975 A | 3/1997 | Liang et al. |
| 5,779,688 A | 7/1998 | Imran et al. |
| 5,813,997 A | 9/1998 | Imran et al. |
| 5,844,140 A | 12/1998 | Seale |
| 5,853,368 A | 12/1998 | Solomon et al. |
| 5,873,906 A | 2/1999 | Lau et al. |
| 5,938,623 A | 8/1999 | Quiachon et al. |
| 5,938,671 A | 8/1999 | Katoh et al. |
| 5,968,064 A | 10/1999 | Selmon et al. |
| 6,004,330 A | 12/1999 | Middleman et al. |
| 6,068,638 A | 5/2000 | Makower |
| 6,110,121 A | 8/2000 | Lenker |
| 6,157,852 A | 12/2000 | Selmon et al. |
| 6,200,269 B1 | 3/2001 | Lin et al. |
| 6,235,000 B1 | 5/2001 | Milo et al. |
| 6,241,667 B1 | 6/2001 | Vetter et al. |
| 6,241,744 B1 | 6/2001 | Imran et al. |
| 6,296,615 B1 | 10/2001 | Brockway |
| 6,306,097 B1 | 10/2001 | Park et al. |
| 6,409,669 B1 | 6/2002 | Hager et al. |
| 6,500,147 B2 | 12/2002 | Omaleki et al. |
| 6,501,551 B1 | 12/2002 | Tearney et al. |
| 6,547,803 B2 | 4/2003 | Seward et al. |
| 6,572,551 B1 | 6/2003 | Smith et al. |
| 6,592,526 B1 | 7/2003 | Lenker |
| 6,599,304 B1 | 7/2003 | Selmon et al. |
| 6,749,560 B1 | 6/2004 | Konstorum et al. |
| 7,658,715 B2 | 2/2010 | Park et al. |
| 2002/0072669 A1 | 6/2002 | Masters |
| 2002/0107447 A1 | 8/2002 | Suorsa et al. |
| 2003/0055338 A1 | 3/2003 | Steininger et al. |
| 2003/0229286 A1 | 12/2003 | Lenker |
| 2004/0056751 A1 | 3/2004 | Park |
| 2004/0254471 A1 | 12/2004 | Hadjicostis et al. |
| 2006/0173348 A1 | 8/2006 | Wilser et al. |
| 2007/0016062 A1 | 1/2007 | Park et al. |
| 2007/0016063 A1 | 1/2007 | Park et al. |
| 2007/0249937 A1 | 10/2007 | Hasegawa et al. |
| 2007/0287914 A1 | 12/2007 | Cohen |
| 2008/0081947 A1 | 4/2008 | Irion et al. |

FOREIGN PATENT DOCUMENTS

| | | |
|---|---|---|
| WO | WO 98/46119 A | 10/1998 |
| WO | WO 99/40963 A | 8/1999 |
| WO | WO 2004/096049 A2 | 11/2004 |

OTHER PUBLICATIONS

International Search Report and Written Opinion issued on Dec. 1, 2006 for PCT/US2006/017130.
International Search Report and Written Opinion issued on Jun. 12, 2007 for PCT/US2006/033408.
International Preliminary Report on Patentability issued on Jun. 20, 2007 for PCT/US2006/017130.
International Preliminary Report on Patentability issued on Dec. 11, 2007 for PCT/US2006/033408.
Office Action issued on Dec. 24, 2008 for U.S. Appl. No. 11/415,848, filed May 2, 2006.
Korean Intellectual Property Office, International Search Report and the Written Opinion of the International Searching Authority, or the Declaration for PCT/US2010/048122, mailed Apr. 8, 2011, 10 pages.
Korean Intellectual Property Office, "International Search Report and the Written Opinion of the International Searching Authority, or the Declaration" for PCT/US2009/044218, mailed Dec. 29, 2009, 11 pages.
Korean Intellectual Property Office, International Search Report for PCT/US2012/059748, mailed Mar. 19, 2013, 3 pages.

ROTATIONAL SHAPE-MEMORY ACTUATORS AND ASSOCIATED DEVICES, SYSTEMS, AND METHODS

CROSS-REFERENCE TO RELATED APPLICATIONS

This application is a non-provisional patent application that claims priority to and the benefit of U.S. Provisional Patent Application No. 61/546,419, filed Oct. 12, 2011, titled "ROTATIONAL SHAPE MEMORY ACTUATORS AND ASSOCIATED DEVICES, SYSTEMS, AND METHODS," and U.S. Provisional Patent Application No. 61/579,984, filed Dec. 23, 2011, titled "ROTATIONAL SHAPE MEMORY ACTUATORS AND ASSOCIATED DEVICES, SYSTEMS, AND METHODS," each hereby incorporated by reference in its entirety.

TECHNICAL FIELD

The present disclosure relates to rotational actuators and associated devices, systems, and methods. In some embodiments, the rotational actuators are particularly suited for use in intravascular and intracardiac imaging devices, including catheters and guidewires.

BACKGROUND

Heart disease is very serious and often requires emergency operations to save lives. A main cause of heart disease is the accumulation of plaque inside the blood vessels, which eventually occludes the blood vessels. Several treatments are available to open up the occluded vessel (e.g., balloon angioplasty, rotational atherectomy, and intravascular stents). Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray. Intravascular imaging, on the other hand, can be a valuable tool both during interventional procedures as an aid to navigation and for intra-operative feedback and after interventional procedures for post-operative feedback regarding the results of the procedure.

Ultrasonic transducers have been utilized to visualize the inside of the blood vessels. Current ultrasonic transducer devices are mostly based on one or more stationary ultrasound transducers or rotating a single transducer in parallel to the blood vessels by means of a rotating shaft that extends along the length of the device to a motor or other rotary device located outside the patient. The ultrasonic transducer arrangements of these devices require a relatively large amount space inside the device such that overall of diameter of the device cannot be reduced to desired sizes and/or there is not sufficient room within the device to accommodate other desired components. Also, for rotating ultrasound transducer arrangements, the rotating shaft required to facilitate rotation of the ultrasound transducer causes the distal end of the device to be very stiff, which limits the ability of the device to go through tortuous vessels. Also, the high speed rotating shaft also contributes to distorted non-uniform images when imaging a tortuous path in the vasculature, which is commonly referred to as non-uniform rotational distortion (NURD).

Optical coherence tomography (OCT) has also been utilized to visualize the inside of blood vessels based on differential reflectance, but most rely on a rotating fiber optic that extends along the length of the device. This approach also has problems including, for example, implementing the spinning and scanning motion required without damaging a delicate glass or polycarbonate optical fiber. Also, with the actuator mechanism located outside the patient and tip located inside the patient, inefficiencies and control issues arise from the torque created by a long, spinning member. In that regard, remote mechanical manipulation and a long spinning element distort the image due to NURD.

Accordingly, there remains a need for improved devices, systems, and methods for controlling motion of imaging elements within an intravascular imaging device. In that regard, there remains a need for improved rotational actuators sized and shaped for implementation within intravascular imaging devices sized for introduction into human vasculature, including intravascular imaging devices having an outer diameter of 0.018" or less.

SUMMARY

Embodiments of the present disclosure are directed to rotational shape-memory actuators and associated devices, systems, and methods.

In one embodiment, a method of manufacturing an intravascular imaging device is provided. The method includes providing a first anchor and a second anchor; fixedly securing a first shape memory element to the first anchor and the second anchor; fixedly securing a second shape memory element to the first anchor and the second anchor; and rotating the second anchor relative to the first anchor such that the first and second shape memory elements are twisted or braided together. In some instances, the first and second shape memory elements are configured to transition between a first state and a second state such that when the first and second shape memory elements are in the first state the first and second shape memory elements are twisted together and when the first and second shape memory elements are in the second state the first and second shape memory elements are less twisted than in the first state. In that regard, the first state is a martensite state and the second state is an austenite state in some instances. The method further includes fixedly securing a spring to the first anchor and the second anchor in some embodiments. In that regard, the spring may be fixedly secured to the second anchor while the first and second shape memory elements are twisted together. In some embodiments, the length between the first anchor and the second anchor is less than 5 mm and, in some instances, less than 1 mm after the first and second shape memory elements and the spring are secured thereto. In some instances, the method further includes fixedly securing the first anchor to a distal portion of a flexible elongate member sized and shaped for introduction into human vasculature. In that regard, the flexible elongate member may be a catheter, a guidewire, or other instrument. An imaging element, such as an ultrasound transducer or a reflector, is coupled to the second anchor in some instances. In some instances, the method further includes fixedly securing a third shape memory element to the first anchor and the second anchor such that rotating the second anchor relative to the first anchor causes the first, second, and third shape memory elements to be twisted or braided together. In some instances, the method further includes fixedly securing a single shape memory element to the first anchor and the second anchor such that rotating the second anchor relative to the first anchor causes the single shape memory elements to be twisted.

In another embodiment, a rotational actuator is provided. The rotational actuator includes a first anchor; a second anchor; a spring element extending between the first and second anchors; a first shape memory element extending between the first and second anchors; and a second shape memory element extending between the first and second anchors. The first and second shape memory elements are configured to transition between a first state and a second state such that when the first and second shape memory elements are in the first state the first and second shape memory elements are in a first configuration in which the first and second shape memory elements are twisted together and when the first and second shape memory elements are in the second state the first and second shape memory elements are in a second configuration in which the first and second shape memory elements are less twisted together than in the first configuration. Transitions of the first and second shape memory elements between the first and second states cause the second anchor to rotate about a longitudinal axis with respect to the first anchor. In some instances, the first and second shape memory elements are positioned within a lumen defined by the spring element. In some configurations, the spring element is configured to urge the first and second shape memory elements towards the first configuration. In some embodiments, the first anchor includes an inner conductive portion, an outer conductive portion, and an insulating portion positioned between the inner and outer conductive portions to conductively isolate the inner and outer conductive portions from one another. In some instances, proximal portions of the first and second shape memory alloy elements are conductively coupled to the inner conductive portion of the first anchor. Also, in some instances the spring is conductively coupled to the outer conductive portion of the first anchor.

In yet another embodiment, an intravascular or intracardiac imaging device is provided. The intravascular imaging device includes: an elongate flexible member having a proximal portion and a distal portion and an actuator secured to the distal portion of the elongate flexible member. The actuator includes: a first anchor fixedly secured to the elongate flexible member; a second anchor spaced distally along a longitudinal axis of the elongate flexible member from the first anchor; a first shape memory element extending between the first and second anchors; and a second shape memory element extending between the first and second anchors. The first and second shape memory elements are configured to transition between a first state and a second state such that when the first and second shape memory elements are in the first state the first and second shape memory elements are in a first configuration in which the first and second shape memory elements are twisted together and when the first and second shape memory elements are in the second state the first and second shape memory elements are in a second configuration in which the first and second shape memory elements are less twisted together than in the first configuration. Transitions of the first and second shape memory elements between the first and second states cause the second anchor to rotate about the longitudinal axis of the elongate flexible member. In some embodiments, an imaging element is coupled to the second anchor such that the imaging element rotates about the longitudinal axis of the elongate flexible member with the second anchor. In that regard, the imaging element is at least one of an ultrasound transducer and a reflector in some instances.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

Together.

FIG. 4 is a diagrammatic side view illustrating anchors of the rotational actuator according to an embodiment of the present disclosure.

FIG. 5 is a diagrammatic side view illustrating attachment of shape-memory elements to the anchors of FIG. 4 according to an embodiment of the present disclosure.

FIG. 6 is a diagrammatic side view illustrating the positioning of a spring element relative to anchors and shape-memory elements of FIG. 5 and attachment of the spring element to one of the anchors according to an embodiment of the present disclosure.

FIG. 7 is a diagrammatic side view illustrating rotation of one of the anchors relative to the other about a longitudinal axis of the rotational actuator according to an embodiment of the present disclosure.

FIG. 8 is a diagrammatic side view illustrating attachment of the spring element to the other anchor according to an embodiment of the present disclosure.

DETAILED DESCRIPTION

Figure 1:
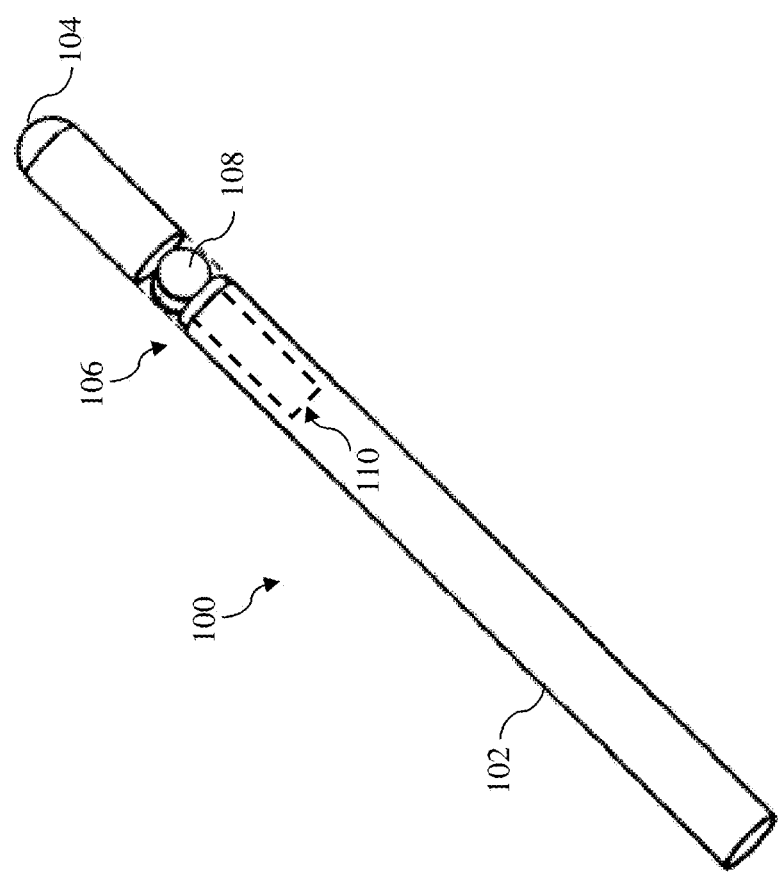
FIG. 1 is a diagrammatic perspective view of a portion of an intravascular imaging device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In some aspects, embodiments of the present disclosure relate to imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques. Two of the most common are the use of ultrasound energy, commonly known as intravascular ultrasound (IVUS) and optical coherence tomography (OCT). Embodiments of each of these techniques rely on the imaging device being repeatedly swept, oscillated, or rotated to obtain data suitable for creating an image of the vessel.

To address the limitations of current devices, new rotational actuators for use in intravascular imaging devices are described below. In that regard, the rotational actuators of the present disclosure utilize one or more Shape Memory Alloy (SMA) elements to impart rotational motion to an imaging element coupled to the actuator. In some instances, the actuators provide side-looking imaging by rotating the imaging element about a longitudinal axis of a flexible elongate member to which the actuator is coupled. In that regard, the small dimensions of the actuators of the present disclosure allow for the diameter of the flexible elongate member to also be very small. For example, the outside diameter of the elongate member, such as a guidewire or catheter, containing a rotational actuator and an imaging element as described herein are between about 0.0007" (0.0178 mm) and about 0.118" (3.0 mm), with some particular embodiments have outer diameters of approximately 0.014" (0.3556 mm) and approximately 0.018" (0.4572 mm)). As such, the flexible elongate members incorporating the actuators and imaging arrangements of the present application are suitable for use in a wide variety of lumens within a human patient besides those that are part or immediately surround the heart, including atriums, ventricles, veins and arteries of the extremities, renal arteries, blood vessels in and around the brain, and other lumens.

Further, the small dimensions of the actuators of the present disclosure allow room within the flexible elongate member for incorporation of the components of one or more additional interventional devices (e.g., guide wires, pressure sensors, temperature sensors, imaging elements, optical fibers, ultrasound transducers, reflectors, mirrors, prisms, ablation elements, rf electrodes, conductors, etc.) to be included along with the imaging element. Also, because the rotating actuators of the present disclosure do not require a rotating shaft or fiber optic cable to extend proximally along the length of the flexible elongate member, the actuators allow the elongate member to have increased flexibility if desired. In addition, the lack of rotating shaft extending along the length of the flexible elongate member eliminates many of the problems associated with NURD.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, intravascular catheters and intravascular guidewires. In that regard, intravascular catheters may or may not include a lumen extending along its length for receiving and/or guiding other instruments. If the intravascular catheter includes a lumen, the lumen may be centered or offset with respect to the cross-sectional profile of the device.

The rotating actuator mechanisms of the present disclosure are typically disposed within a distal portion of the flexible elongate member. As used herein, "distal portion" of the flexible elongate member includes any portion of the flexible elongate member from the mid-point to the distal tip. As flexible elongate members can be solid, some will include a housing portion at the distal portion for receiving the actuators of the present disclosure. Such housing portions can be tubular structures attached to the distal portion of the elongate member. Some flexible elongate members are tubular and have one or more lumens in which the actuator can be positioned within the distal portion.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Movements that are described as "counter" herein are movements in the opposite direction of an initial movement. For example, if an element is rotated clockwise about a longitudinal axis, then rotation in a counterclockwise direction about the longitudinal axis is a movement that is "counter" to the clockwise rotation. Similarly, if the element is moved substantially parallel to the longitudinal axis in a distal direction, then movement substantially parallel to the longitudinal axis in a proximal direction is "counter" to the distal direction movement.

"Reflector" as used herein encompasses any material which reflects or refracts a substantial portion of ultrasound or light energy directed at it. In some embodiments of the present disclosure, the reflector is a mirror. In other embodiments, the reflector is a prism.

Referring now to FIG. 1, shown therein is a portion of an intravascular imaging device 100 according to an embodiment of the present disclosure. In that regard, the intravascular imaging device 100 includes a flexible elongate member 102 having a distal tip 104. An imaging arrangement 106 is positioned within a distal portion of the flexible elongate member 102 proximal of the distal tip 104. In some instances, the imaging arrangement 106 is positioned less than 10 cm, less than 5, or less than 3 cm from the distal tip. In some instances, the imaging arrangement 106 is positioned within a housing of the flexible elongate member 102. In that regard, the housing is a separate component secured to the flexible elongate member 102 in some instances. In other instances, the housing is integrally formed as a part of the flexible elongate member 102.

The imaging arrangement 106 includes an imaging element 108 that is coupled to a rotational actuator 110. The rotational actuator 110 is configured to rotate the imaging element 108 about the longitudinal axis of the flexible elongate member. In that regard, the rotational actuator 110 is configured to rotate the imaging element about the longitudinal axis between about 5 degrees and about 720 degrees. In some particular embodiments, the rotational actuator 110 is configured to rotate the imaging element about the longitudinal axis about 360 degrees. Imaging element 108 is representative of a component of an ultrasound, OCT, infrared, thermal, or other imaging modality, which includes such components as imaging transducers, ultrasound transducers, optical fibers, reflectors, and/or other imaging components. In some instances, the imaging element 108 is arranged to emit and/or reflect energy (e.g., ultrasound, light, etc.) in a direction generally perpendicular to the longitudinal axis of the flexible elongate member. In other instances, the imaging element 108 is arranged to emit and/or reflect energy at an oblique angle between 15 degrees and about 165 degrees, with the preferred angle for side-looking being between about 80 degrees and about 110 degrees. Angles contemplated include about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, and about 165 degrees, or can fall within a range between any two of these values.

Figure 2:
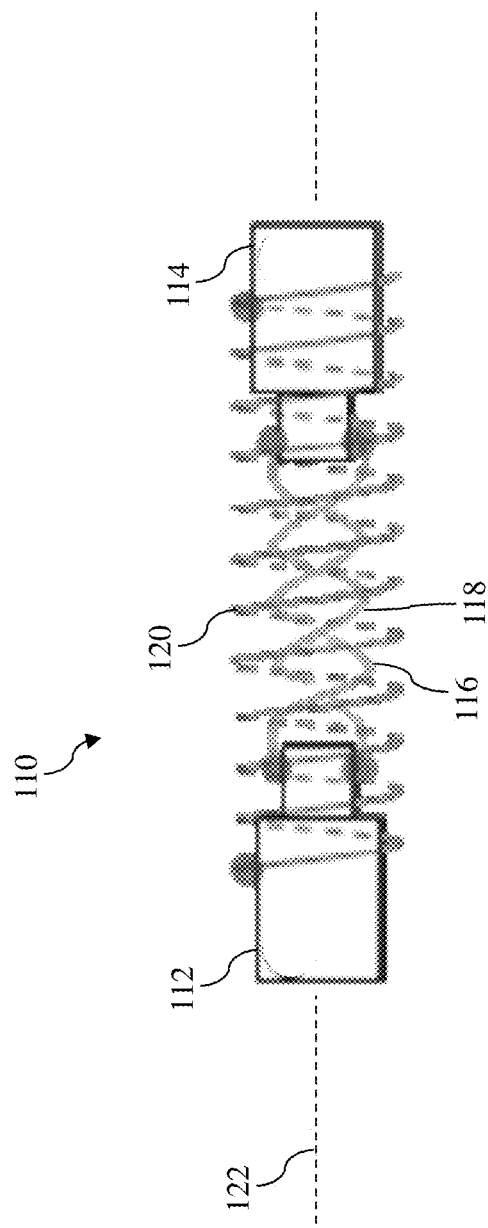
FIG. 2 is a diagrammatic side view of a rotational actuator according to an embodiment of the present disclosure in a first orientation.
Figure 3:
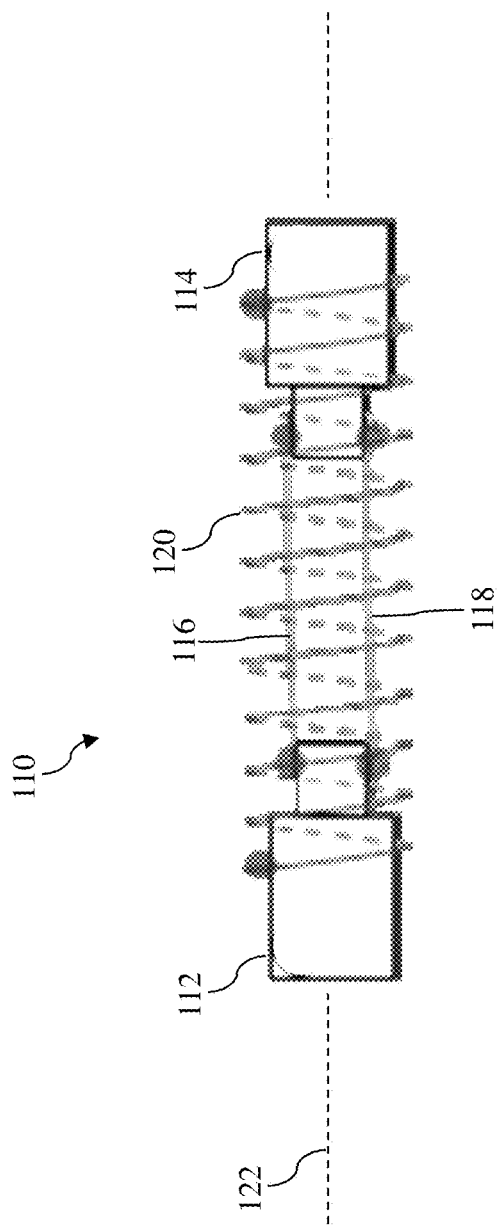
FIG. 3 is a diagrammatic side view of the rotational actuator of FIG. 2, but illustrating the rotational actuator in a second orientation.

Referring now to FIGS. 2 and 3, shown therein are aspects of the rotational actuator 110. In that regard, FIG. 2 shows the rotational actuator 110 in a first, twisted orientation and FIG. 3 shows the rotational actuator 110 in a second, untwisted orientation. As shown, the rotational actuator includes an anchor 112 and an anchor 114. A pair of shape-memory elements 116 and 118 extend between and are secured to the anchors 112 and 114. In FIG. 2, the shape-memory elements 116 and 118 are twisted together, while in FIG. 3 the shape-memory elements 116 and 118 are untwisted. As discussed in greater detail below, transitions between the twisted and untwisted (or less twisted) orientations of the shape-memory elements 116 and 118 drive the rotational motion of the actuator 110 and, in turn, the imaging element 108. In that regard, in some embodiments, the anchor 112 is configured to be fixedly secured to the flexible elongate member 102 while the anchor 114 is able to rotate with respect to the flexible elongate member 102. Accordingly, with the imaging element 108 secured to the anchor 114, rotation of the anchor 114 caused by the shape-memory elements 116 and 118 of the rotational actuator 110 will also cause rotation of the imaging element 108.

The shape-memory elements 116 and 118 can be fabricated from any known material with shape memory characteristics. In some embodiments, the shape-memory elements of the present disclosure are formed of nitinol. In some embodiments, the shape-memory elements are a nitinol wire having a diameter between about 0.010" (0.254 mm) and about 0.0005" (0.0127 mm). In one particular embodiment, the shape-memory elements are nitinol wires having a diameter of about 0.001" (0.0254 mm). Shape-memory elements can be fabricated to take on a predetermined shape when activated. Often activation of a shape-memory element consists of heating the shape-memory element such that it adopts its trained shape. In some embodiments of the present disclosure, this is accomplished by applying an electric current across the shape-memory elements. In that regard, in some embodiments two or more conductors extend along the length flexible elongate member to apply electrical current to the shape-memory elements to facilitate activation of the shape-memory elements. Activation of the shape-memory elements to cause a deformation to their trained shape can impart a force that can be utilized to cause rotational movement. For example, as shown in FIG. 3, the shape-memory elements 116 and 118 have been trained to have a straightened orientation in their activated state (e.g., austenite state). Accordingly, by activating (e.g., heating) the shape-memory elements 116 and 118, the shape-memory elements 116 and 118 will transition from the twisted orientation of FIG. 2 to the untwisted or straightened orientation of FIG. 3. This transition causes rotation of the anchor 114 relative to the anchor 112.

Deactivation of a shape-memory element is often achieved by turning off current to the shape-memory element such that the shape-memory element returns to its pliable state as it cools. In that regard, the rotational actuator 110 also includes a bias element 120. The bias element 120 is configured to bias the shape-memory elements 116 and 118 towards the twisted configuration of FIG. 2. In that regard, the bias element 120 is coupled to the anchors 112 and 114 such that as the anchor 114 rotates relative to the anchor 112 upon activation of the shape-memory elements 116 and 118, potential energy will be stored in the bias element 120. Accordingly, as the shape-memory elements 116 and 118 cool and return to their pliable state (e.g., martensite state) the potential energy stored in the bias element 120 will impart a rotational force on the shape-memory elements 116 and 118 that causes them to return to the twisted orientation of FIG. 2.

Accordingly, by selectively activating and deactivating the shape-memory elements 116 and 118, repeated rotational movement will be imparted upon anchor 114 relative to anchor 112. In that regard, as the shape-memory elements 116 and 118 transition from the twisted orientation of FIG. 2 to the untwisted orientation of FIG. 3 (as a result of activation of the shape-memory elements), the anchor 114 is rotated in a first direction (e.g., clockwise or counter-clockwise) relative to the anchor 112 about the longitudinal axis 122. Then, as the shape-memory elements 116 and 118 transition from the untwisted orientation of FIG. 3 to the twisted orientation of FIG. 2 (as a result of deactivation, or cooling, of the shape-memory elements and the force of bias element 120), the anchor 114 is rotated in a second direction that is counter to the first direction (e.g., counter-clockwise or clockwise) relative to the anchor 112 about the longitudinal axis 122. In that regard, the amount of rotation between the twisted and untwisted orientations is generally between about 5 degrees and about 720 degrees. However, in other embodiments, the amount of rotation is less than 5 degrees or more than 720 degrees. In some particular embodiments, the amount of rotation between the first and second orientations of the shape-memory elements 116 and 118 is about 360 degrees. In some particular embodiments, the shape memory elements is partially activated via current or heat in order for the shape memory elements to achieve and hold a specific twist level or scan angle. The amount of heat or current passing through the shape-memory elements balances the heat lost due to passive cooling such that a specific twist configuration or scan angle is maintained. This can be useful when a specific scan angle needs to be monitored continuously as a function of time.

While the shape-memory elements are shown as being twisted in FIG. 2 and untwisted in FIG. 3, this is merely for simple illustration of the underlying concept. It is understood that in other embodiments the shape-memory elements 116 and 118 transition between two twisted orientations where the first twisted orientation has more twists than the second twisted orientation. Further still, in some embodiments the activated state of the shape-memory elements corresponds to a twisted orientation and the deactivated state corresponds to an untwisted or less twisted orientation.

The bias element 120 provides several important functions in some embodiments. First, as discussed above, the bias element 120 provides the counterbalance force that re-twists the shape-memory elements 116 and 118 as the shape-memory elements passively cool to the lower-temperature martensite state. Second, the bias element keeps the actuator 110 taught between the anchor 112 and the anchor 114, preventing the twisted shape-memory elements 116 and 118 from collapsing into a ball. In this sense, the bias element provides a structural integrity to the actuator 110. In mathematical terms, or topologically, the bias element 120 helps the actuator 110 maintain its twist value and prevents the shape-memory elements from converting the twist to writhe. Finally, the bias element 120 protects the shape-memory elements 116 and 118 from physical contact with other parts and liquids. In that regard, the bias element 120 serves as a scaffold or base structure for an insulating layer (e.g., polyimide tubing) for a further improved level of electrical and liquid insulation.

In the illustrated embodiment, the bias element 120 is a spring. The spring material, diameter, pitch, and length are selected to minimize the size of the actuator while providing the necessary return force and structural integrity to the actuator. In some instances, the spring is formed of one or more of copper, beryllium copper, aluminum, stainless steel, tungsten, brass, or other suitable material. In that regard, the radius (or other cross-sectional measurement for non-circular cross-sectional profiles) of the wire utilized to form the spring is between about 0.0003" (0.00762 mm) and about 0.003" (0.0762 mm). In some embodiments, the spring has a diameter between about 0.005" (0.127 mm) and about 0.0393" (1 mm), a length between about 0.0196" (0.5 mm) and about 0.196" (5 mm), and a pitch between about the thickness of the wire and about 0.0784" (2 mm). As a general matter, the spring is stiffer when the spring diameter is decreased, the spring length is decreased, the spring pitch is increased, the radius of the wire used to create the spring is increased, and/or the wire material chosen to create the spring has a higher torsional stiffness.

While the bias element 120 has been illustrated and described as being a coil spring, it is understood that the bias element 120 may be any device (or combination of devices) capable of performing the functions of bias element 120 described above. In some instances, the bias element 120 is made from materials that are not rigid, including elastic, superelastic, and non-elastic materials. Suitable materials include trained and untrained shape-memory alloys including but not limited to nitinol; elastic alloys including but not limited to stainless steel and titanium alloy; and superelastic alloys including but not limited to Cu—Al—Ni, Cu—Al, Cu—Zn—Al, Ti—V, and Ti—Nb alloy.

Figure 4:
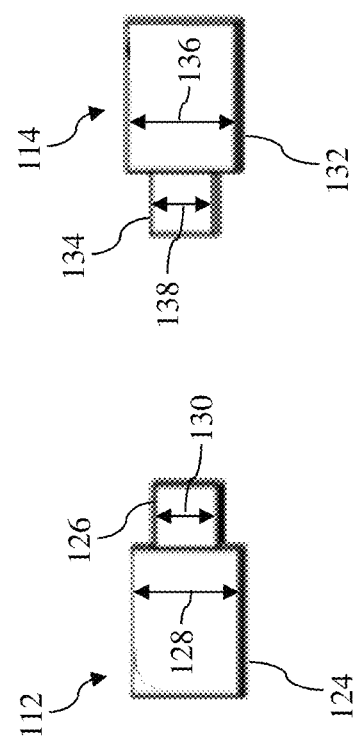
FIGS. 4-8 illustrate a method of assembling the rotational actuator of FIGS. 2 and 3.

Referring now to FIGS. 4-8, shown therein are aspects of a method of assembling the rotational actuator 110 according to one embodiment of the present disclosure. As shown in FIG. 4, the anchors 112 and 114 are provided. In that regard, anchor 112 includes a primary body portion 124 and an extension 126. As shown, the primary body portion 124 has a diameter 128. In some instances, the diameter 128 is between about 0.005" (0.127 mm) and about 0.0393" (1 mm). The extension 126 has a diameter 130 that is less than the diameter 128 of the primary body portion 124. In some instances, the diameter 130 is between about 0.002" (0.051 mm) and about 0.0373" (0.95 mm). Similarly, in some instances the diameter 130 is between about 10% and about 95% of the diameter 128. Generally, the extension 126 serves as an anchor point for the proximal portions of the shape-memory elements extending between the anchors 112 and 114. Accordingly, the extension 126 can have any of a variety of geometrical profiles, non-geometrical profiles, and/or combinations thereof. Extension 126 may also have one or more guidance slots, holes, openings, or other structural features that are used for the positioning of the shape memory elements relative to the extension. The structural feature(s) may or may not be spaced equally around the circumference of extension 126. In the case of a single shape memory element actuator, a hole at the center of extension 126 may be used to position shape memory element at the center of extension 126.

Similarly, anchor 114 includes a primary body portion 132 and an extension 134. As shown, the primary body portion 132 has a diameter 136. In some instances, the diameter 136 is between about 0.005" (0.127 mm) and about 0.0393" (1 mm). The extension 134 has a diameter 138 that is less than the diameter 136 of the primary body portion 132. In some instances, the diameter 138 is between about 0.002" (0.051 mm) and about 0.0373" (0.95 mm). Similarly, in some instances the diameter 138 is between about 10% and about 95% of the diameter 136. Generally, the extension 134 serves as an anchor point for the distal portions of the shape-memory elements extending between the anchors 112 and 114. Accordingly, the extension 134 can have any of a variety of geometrical profiles, non-geometrical profiles, and/or combinations thereof. In the illustrated embodiment, the anchor 114 is shown as being substantially identical in size and shape as the anchor 112. In other embodiments, the anchors 112 and 114 have one or more different characteristics. Extension 134 may also have one or more guidance slots, holes, openings, or other structural features that are used for the positioning of the shape memory elements relative to the extension. The structural feature(s) may or may not be spaced equally around the circumference of extension 134. In the case of a single shape memory element actuator, a hole at the center of extension 134 may be used to position shape memory element at the center of extension 134.

As shown in FIG. 4, the anchors 112 and 114 are positioned such that the extensions 126 and 134 extend towards one another. In some instances, the anchor 112 is configured to be positioned proximal of the anchor 114 when attached to the flexible elongate member 102. Accordingly, anchor 112 may be considered to be positioned proximal of the anchor 114 such that the extension 126 of anchor 112 is positioned distally towards anchor 114 and the extension 134 of anchor 114 is positioned proximally towards anchor 112.

Figure 5:
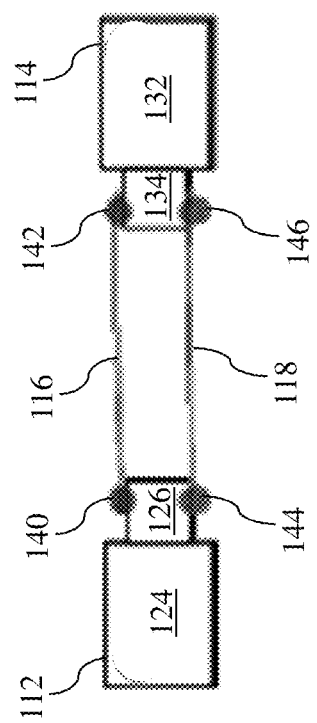

Referring now to FIG. 5, the shape-memory element 116 is secured to the extension 126 of anchor 112 by connection 140 and secured to the extension 134 of anchor 114 by connection 142. Similarly, the shape-memory element 118 is secured to the extension 126 of anchor 112 by connection 144 and secured to the extension 134 of anchor 114 by connection 146. In that regard, the connections 140, 142, 144, and 146 are representative of any suitable manner of fixedly securing the shape-memory elements 116 and 118 to the anchors 112 and 114. In some instances, the connections 140, 142, 144, and 146 are one or more of a weld, an adhesive, a mechanical coupling, and/or combinations thereof. As shown, in the illustrated embodiment the shape-memory elements 116 and 118 are secured to the anchors 112 and 114 such that they extend relatively straight across between the anchors. In some embodiments, this straight configuration of the shape-memory elements 116 and 118 is an activated or austenite state (i.e., a trained shape of the material) of the shape-memory elements. In other embodiments, this straight configuration of the shape-memory elements 116 and 118 is a deformed martensite state of the shape-memory elements.

Figure 6:
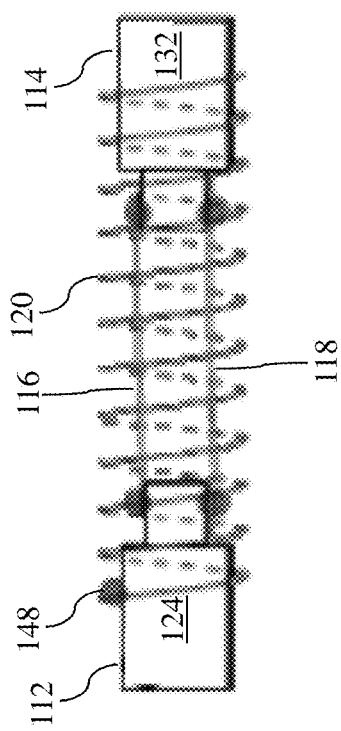

Referring now to FIG. 6, the bias element 120 is positioned over the anchors 112 and 114 and the shape-memory elements 116 and 118. With the bias element 120 positioned over the anchors 112 and 114 and the shape-memory elements 116 and 118, as shown, the bias element 120 is secured to the primary body portion 124 of anchor 112 by connection 148. The connection 148 is representative of any suitable manner of fixedly securing the bias element 120 to the anchor 112. In some instances, the connection 148 is one or more of a weld, an adhesive, a mechanical coupling, and/or combinations thereof.

Figure 7:
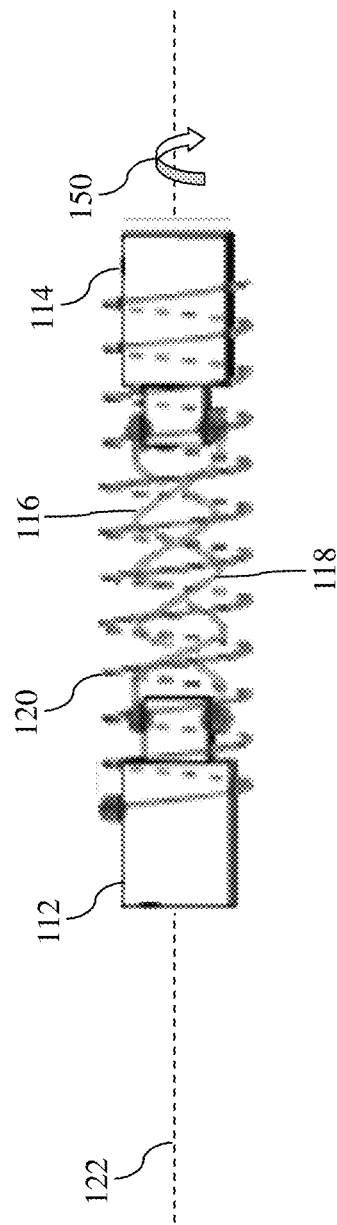

Referring now to FIG. 7, with the bias element secured only to anchor 112, anchor 114 is rotated about the longitudinal axis 122 of the actuator as indicated by arrow 150. Generally, the rotation of the anchor 114 can be in either the clockwise or counter-clockwise direction as view along the longitudinal axis 122 from a position distal of the anchor 114. Arrow 150 illustrates a counter-clockwise rotation. As shown, the rotation of anchor 114 causes the shape-memory elements 116 and 118 to twist together. Because the bias element 120 is not connected to the anchor 114 it is not affected by the rotation of the anchor 114.

Figure 8:
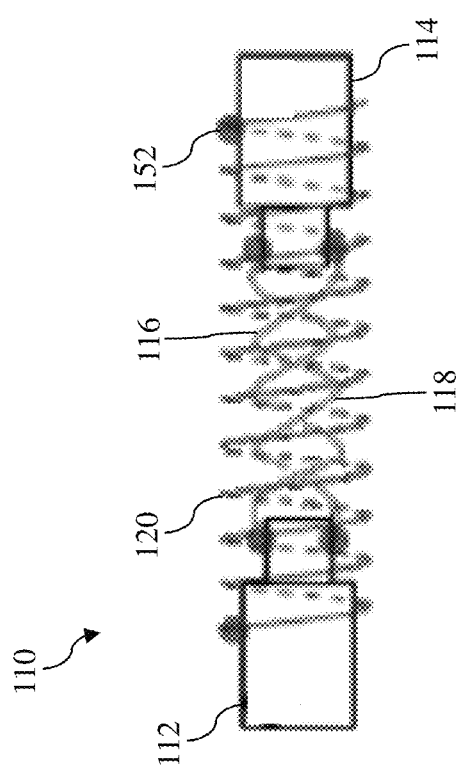

Referring now to FIG. 8, while maintaining the anchor 114 in the rotated position of FIG. 7 such that the shape-memory elements are twisted together, the bias element 120 is secured to the primary body portion 132 of anchor 114 by connection 152. The connection 152 is representative of any suitable manner of fixedly securing the bias element 120 to the anchor 114. In some instances, the connection 152 is one or more of a weld, an adhesive, a mechanical coupling, and/or combinations thereof. With the bias element 120 secured to anchor 114, the actuator 110 is operationally assembled. In that regard, activation and deactivation of the shape-memory elements 116 and 118 will cause the anchor 114 to rotate about the longitudinal axis of the actuator 110 with respect to anchor 112 as discussed above. The assembled actuator 110 has outer diameter between about 0.005" (0.127 mm) and about 0.0393" (1 mm), in some instances. In some particular embodiments, the assembled actuator has an outer diameter of 0.009", 0.011", 0.015", 0.022", 0.028", or 0.031". In that regard, in some implementations an actuator with an outer diameter of 0.009" is suitable for use in a 0.011" guide wire, an 0.011" outer diameter is suitable for use in a 0.014" guide wire, an 0.015" outer diameter is suitable for use in a 0.018" guide wire, an 0.022" outer diameter is suitable for use in a 0.025" guide wire, an 0.028" outer diameter is suitable for use in a 0.032" guide wire, an 0.031" outer diameter is suitable for use in a 0.035" guide wire, and so on with larger sizes. Generally, the outer diameter of the assembled actuator is less than or equal to the outer diameter of the device (e.g., guide wire, catheter, etc.) into which it is incorporated.

With the actuator 110 assembled, the anchor 112 is secured to a flexible elongate member 102 and an imaging element 108 is secured to anchor 114. As a result, the actuator 110 is able to selectively rotate the imaging element 108 relative to the flexible elongate member 102 through the transitions of the shape-memory elements 116 and 118 that cause rotation of the anchor 114. In an alternative embodiment, the anchor 112 is eliminated and the proximal portions of the shape-memory elements 116 and 118 are secured directly to the flexible elongate member (or a housing that is secured to the flexible elongate member). Likewise, in some embodiments, anchor 114 is eliminated and the distal portions of the shape-memory elements 116 and 118 are secured directly to the imaging element 108. In other instances, one or more intermediate components are positioned between the proximal and/or distal portions of the shape-memory elements 116 and 118 and the flexible elongate member 102 and the imaging element 108.

In addition, while FIGS. 2 and 3 show two shape-memory elements (116 and 118) in other embodiments a single shape-memory element is used. Using a single shape-memory allows a further reduction in size of the actuator. In yet other embodiments, three or more shape-memory elements are utilized, including three, four, five, six, seven, eight, nine, and ten shape-memory elements. In that regard, as the number of shape-memory elements is increased, the resulting rotation of the actuator becomes more powerful and faster. Accordingly, the number of shape-memory elements can be selected based on the load of the device or element that is to be rotated by the actuator in some instances.

Generally, the shape-memory elements are arranged symmetrically as they extend between the anchors 112 and 114. In some instances, the shape-memory elements are arranged symmetrically about a circumference such that with two shape-memory elements they are spaced apart by 180 degrees, with three shape-memory elements they are spaced apart by 120 degrees, with four shape-memory elements they are spaced apart by 90 degrees, and so on. In other instances, the shape-memory elements are arranged symmetrically, but not about a common circumference. For example, with four shape-memory elements, one shape-memory element could be centered about a longitudinal axis of the actuator while the remaining three shape-memory elements are equally spaced apart by 120 degrees around a circumference spaced from the centered element. In yet other embodiments, the shape-memory elements are arranged non-symmetrically as they extend between the anchors 112 and 114.

Figure 9:
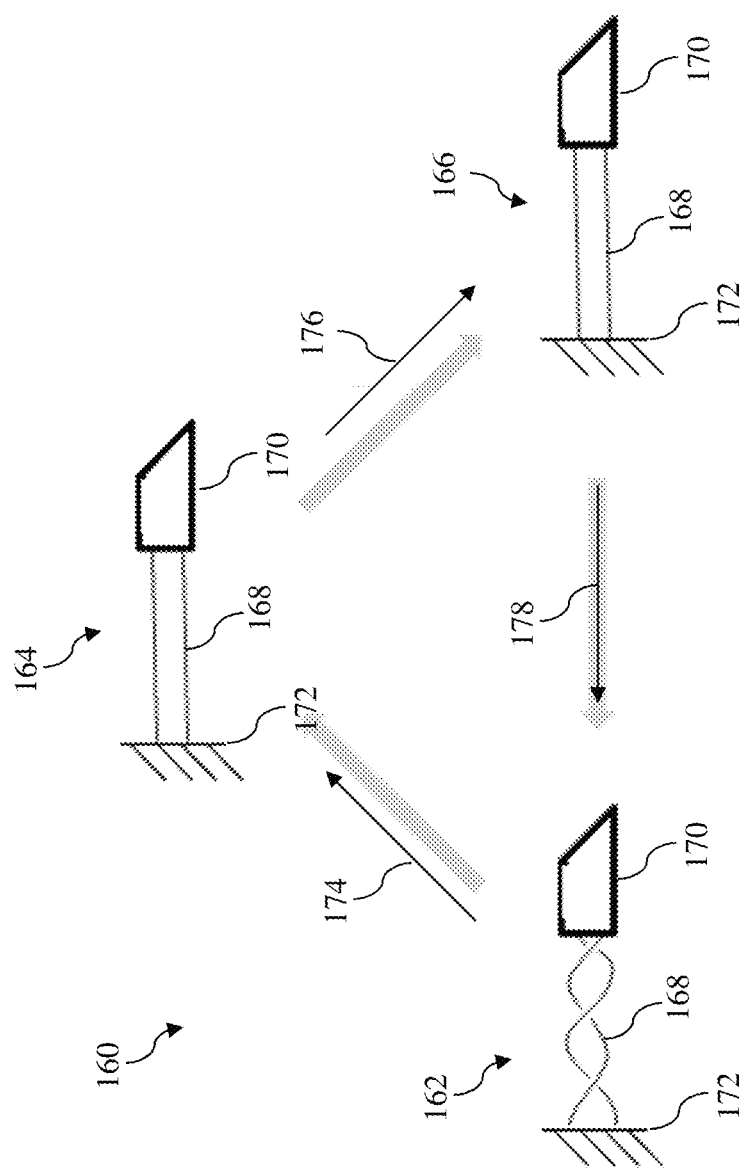
FIG. 9 is a collection of three diagrammatic, schematic views of a shape-memory rotational actuator arrangement illustrating transitions between different states according to an embodiment of the present disclosure.

Referring now to FIG. 9, shown therein is a collection 160 of three diagrammatic, schematic views 162, 164, and 166 of a shape-memory rotational actuator arrangement illustrating transitions between different states of the shape-memory elements according to aspects of the present disclosure. As shown, the actuator includes one or more shape-memory elements 168 and a structure 170 fixedly coupled to a distal portion of the shape-memory elements 168. A proximal portion of the shape-memory elements 168 is fixedly coupled to a structure 172 that is also configured to selectively apply a current to the shape-memory elements for selectively activating and deactivating the shape-memory elements. In that regard, view 162 shows the shape-memory elements 168 in a deformed martensite state where the shape-memory elements are twisted. Arrow 174 represents an application of current to the shape-memory elements 168 that results in a transition of the shape-memory elements 168 to an austenite state (i.e., a trained shape of the material), as shown in view 164. Though not shown, the untwisting of the shape-memory elements 168 causes twisting of the bias element, which causes potential energy to be stored in the bias element. Arrow 176 then represents ceasing application of current to the shape-memory elements 168 that results in a transition of the shape-memory elements 168 to a non-deformed martensite state (i.e., the material is still in the trained shape, but has become deformable) as shown in view 166. Arrow 178 then represents the application of the potential energy stored in the bias element (created from the untwisting of the shape-memory elements in the transition associated with arrow 174) being transferred to the shape-memory elements 168, which causes the shape-memory elements 168 to twist back to the deformed martensite state of view 162. In some instances, the transitions associated with arrows 176 and 178 will occur in quick succession or virtually simultaneously. However, the steps have been described separately to help facilitate a full understanding of the shape-memory transitions utilized to generate the rotational movement of the actuators of the present disclosure.

Figure 10:
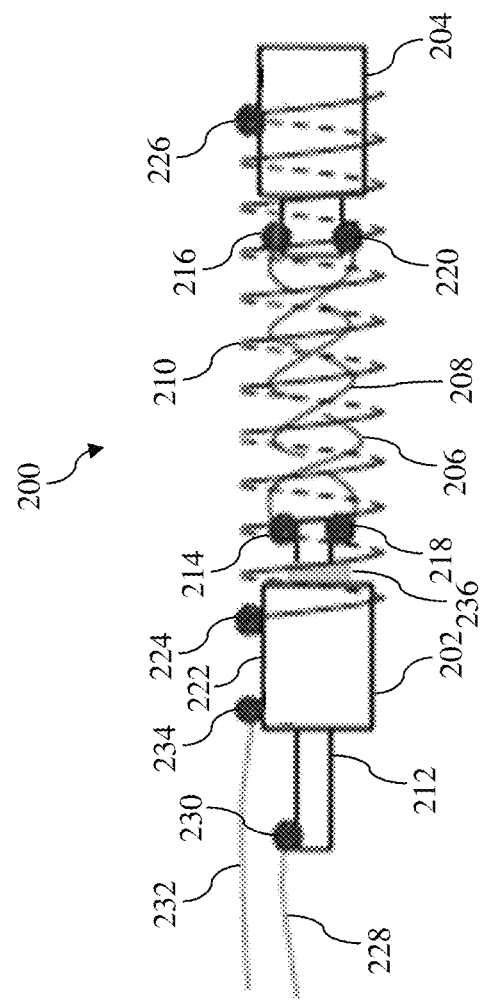
FIG. 10 is a diagrammatic side view of a rotational actuator according to another embodiment of the present disclosure in a first orientation.
Figure 11:
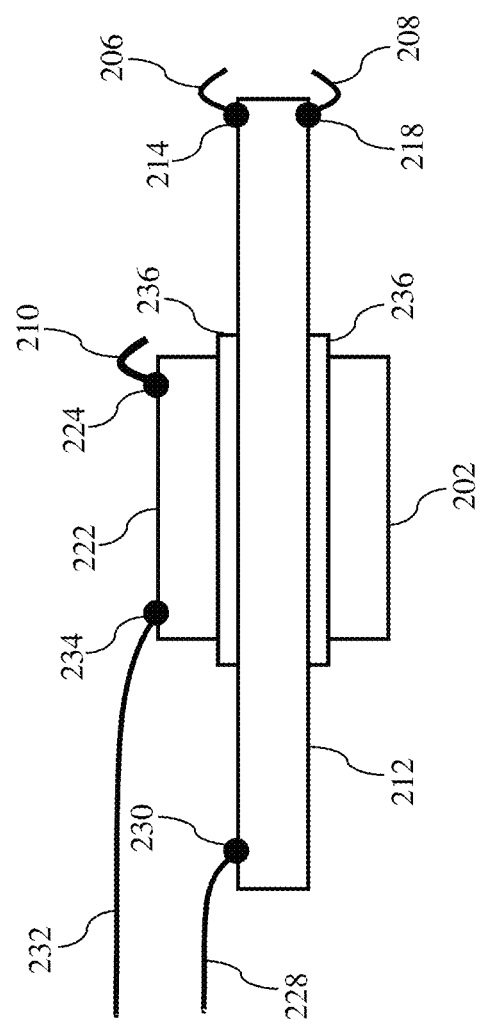
FIG. 11 is a diagrammatic cross-sectional side view of a portion of the rotational actuator of FIG. 10 according to another embodiment of the present disclosure.

Referring now to FIGS. 10 and 11, shown therein are aspects of a rotational actuator 200 according to another embodiment of the present disclosure. The rotational actuator 200 includes many features similar to rotational actuator 110 discussed above. Accordingly, those features will not be discussed in detail here, please refer to the description above. However, the rotational actuator 200 includes a conductive pathway that is particularly suited to facilitate the application of current to the shape-memory elements of the actuator 200. As shown, the rotational actuator 200 includes an anchor 202 and an anchor 204. A pair of shape-memory elements 206 and 208 extend between and are secured to the anchors 202 and 204. Also, a bias element 210 extends between and is secured to the anchors 202 and 204. As discussed above, transitions between the twisted and un-twisted (or less twisted) orientations of the shape-memory elements 206 and 208 (caused by activating and deactivating the shape-memory elements) drive the rotational motion of the actuator 200 and, in turn, an imaging element coupled to the actuator. In that regard, in some embodiments, the anchor 202 is configured to be fixedly secured to a flexible elongate member while the anchor 204 is able to rotate with respect to the flexible elongate member. Accordingly, with the imaging element secured to the anchor 204, rotation of the anchor 204 caused by the shape-memory elements 206 and 208 of the rotational actuator 200 will also cause rotation of the imaging element.

The shape-memory elements 206 and 208 and the bias element 210 are electrically coupled to the anchors 202 and 204 in a manner that facilitates selective application of current to the shape-memory elements 206 and 208 to selectively activate and deactivate the shape-memory elements. In that regard, a proximal portion of the shape-memory element 206 is secured to a conductive inner portion 212 of the anchor 202 by connection 214. In some instances, the inner portion 212 is core wire formed of a conductive material. For example, in one embodiment the inner portion 212 is a wire having a diameter between about 0.002" (0.051 mm) and about 0.0373" (0.95 mm). In one particular embodiment, the inner portion is tungsten wire having 0.004" diameter. A distal portion of the shape-memory element 206 is secured to an extension of the anchor 214 by connection 216. Similarly, a proximal portion of the shape-memory element 208 is secured to the inner portion 212 of the anchor 202 by connection 218, while a distal portion of the shape-memory element 208 is secured to the extension of the anchor 204 by connection 220. Bias element 210, which is formed of a conductive material, has a proximal portion that is secured to a conductive outer portion 222 of the anchor 202 by connection 224 and an opposing distal portion that is secured to the anchor 204 by connection 226. A conductor 228 is secured to the inner portion 212 of the anchor 202 by connection 230, while a conductor 232 is secured to outer portion 222 of the anchor 202 by connection 234. In that regard, in some instances outer portion 222 of the anchor 202 is a hypotube having an inner diameter between about 0.003" (0.0762 mm) and about 0.038" (0.97 mm). Conductors 228 and 232 extend proximally along the length a flexible elongate member in some instances. Generally, the connections 214, 216, 218, 220, 224, 226, 230, and 234 are representative of an electrical connection. In some instances, each of the connections 214, 216, 218, 220, 224, 226, 230, and 234 is a weld and/or a mechanical connection. Finally, referring to FIG. 10 and FIG. 11, an insulating layer 236 electrically insulates the inner portion 212 of the anchor 202 from the outer portion 222 of the anchor. In some instances, the insulating layer is formed of polyimide.

As assembled, the actuator 200 provides an electrical path for selectively activating and deactivating the shape-memory elements 206 and 208. In that regard, a current supplied along conductor 228 is passed through inner portion 212 of anchor 202 to the shape-memory elements 206 and 208. The insulating layer 236 ensures the current travels through the shape-memory elements by preventing the current from shorting through to the outer portion 222 of the anchor 202. From the shape-memory elements 206 and 208, the current passes through the anchor 204 to the distal portion of the bias element 210. In that regard, unlike anchor 202 where the inner portion 212 is electrically insulated from the outer portion 222, with anchor 204 the extension and main body are electrically coupled such that current received from the shape-memory elements 206 and 208 at the extension passes through the anchor to the distal portion of the bias element. From there, the current travels along the bias element 210 to the outer portion 222 of the anchor 202 where conductor 232 is also coupled. In that regard, conductors 228 and 232 are configured to extend proximally through a flexible elongate member where they can be coupled to a voltage source for selective applying the current to the shape-memory elements.

Figure 12:
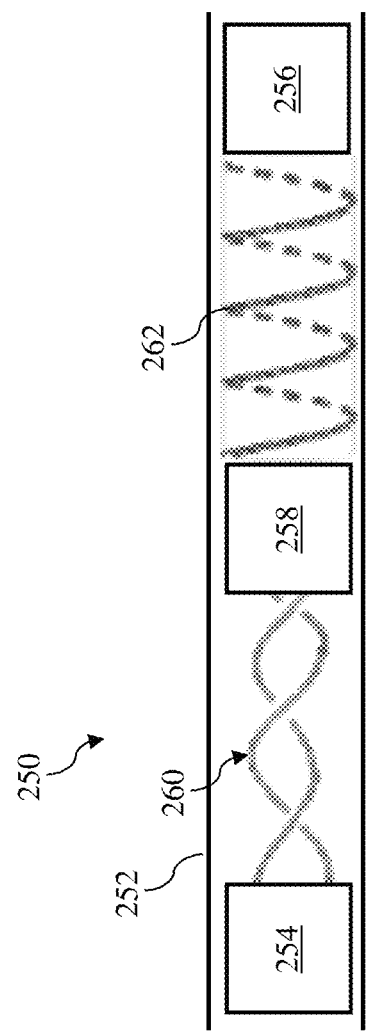
FIG. 12 is a diagrammatic cross-sectional side view of a distal portion of an intravascular imaging device according to an embodiment of the present disclosure showing a rotational actuator of the device in a first orientation.
Figure 13:
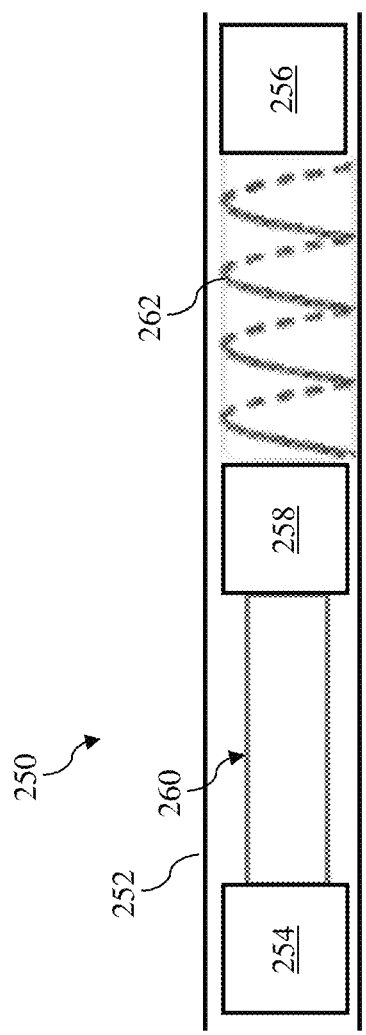
FIG. 13 is a diagrammatic cross-sectional side view of the distal portion of the intravascular imaging device of FIG. 12, but showing the rotational actuator of the device in a second orientation.

Referring now to FIGS. 12 and 13, shown therein is a distal portion 250 of an intravascular imaging device according to another embodiment of the present disclosure. FIG. 12 shows a rotational actuator of the intravascular imaging device 200 in a first twisted orientation, while FIG. 13 shows the rotational actuator in a second untwisted orientation. As shown, the distal portion 250 of the intravascular imaging device includes an outer housing or body 252. An anchor 254 is fixedly secured to the body 252 and an anchor 256 is fixedly secured to the body 252 distal of the anchor 254. Between the anchors 254 and 256 is a structure 258 that is not secured to the body 252. In that regard, the structure 258 is an imaging element in some instances. A plurality of shape-memory elements 260 extend between and are secured to the anchor 254 and the structure 258, while at least one bias element extends between and is secured to the structure 258 and the anchor 256. This arrangement of the anchors 254, 256, shape memory elements 260, and bias element 262 provides a rotational actuator similar to the rotational actuators 110 and 200 discussed above, but where the bias element and the shape-memory elements are positioned in series, rather than having the shape-memory elements positioned within the bias element. The resulting functionality is similar in that transitions between the twisted and un-twisted (or less twisted) orientations of the shape-memory elements 160 drive the rotational motion of the structure 258. In that regard, the bias element 262 is arranged such that as the structure 258 rotates relative to the anchor 254 upon activation of the shape-memory elements 260 (i.e., the transition from FIG. 12 to FIG. 13), potential energy will be stored in the bias element 262. Accordingly, when the shape-memory elements 160 are deactivated and return to their pliable state (e.g., martensite state) the potential energy stored in the bias element 262 imparts a counter rotational force on the shape-memory elements 160 that causes them to return to the twisted orientation of FIG. 12.

Figure 14:
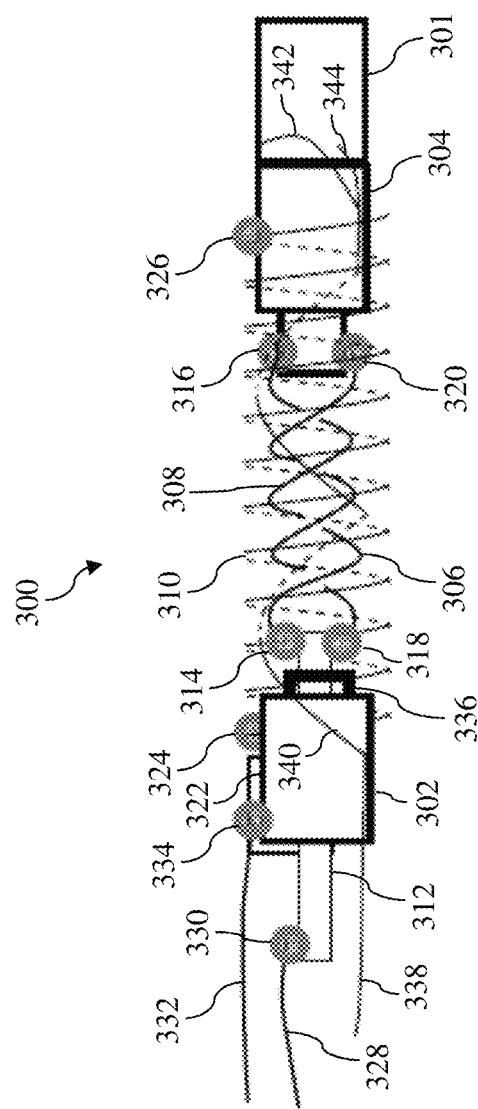
FIG. 14 is a diagrammatic side view of a rotational actuator with an imaging element coupled thereto according to an embodiment of the present disclosure in a first orientation.
Figure 15:
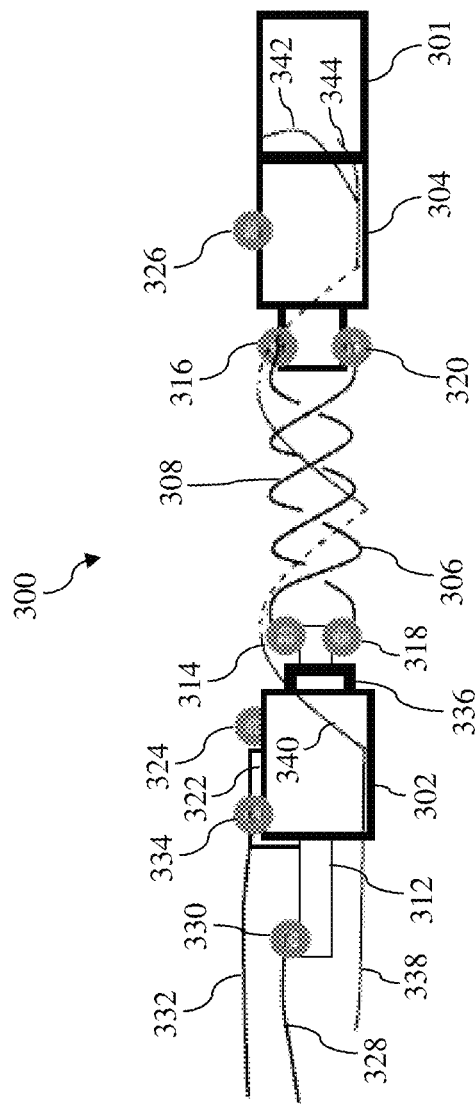
FIG. 15 is a diagrammatic side view of the rotational actuator of FIG. 14, but shown without a bias element to better illustrate an arrangement of communication line(s) extending across the rotational actuator to the imaging element.

Referring now to FIGS. 14 and 15, shown therein are aspects of a rotational actuator 300 according to another embodiment of the present disclosure. The rotational actuator 300 includes many features similar to rotational actuators 110 and 200 discussed above. Accordingly, some of the features described with respect to actuator 110 or actuator 200 will not be discussed in detail here, please refer to the description above. An imaging element 301 is coupled to a distal portion of the rotational actuator 300. In that regard, to function properly the imaging element 301 requires one or more communication lines to extend to it across the rotational actuator 300. In that regard, imaging element 301 is representative of a component of an ultrasound, OCT, infrared, thermal, or other imaging modality, which includes such components as imaging transducers, ultrasound transducers, optical fibers, optical apertures and/or focusing elements, reflectors, other imaging components, and/or combinations thereof. Generally, the imaging element 301 will be an active component of the imaging modality. That is, the imaging element 301 will be configured to send and/or receive signals (e.g., control signals, image data, and/or combinations thereof) over one or more communication pathways to facilitate functioning of the imaging system. In that regard, the limited space within and around the rotational actuator 300 to run such communication lines, the stress on the connections of such communication lines and/or the communication lines themselves as a result of the rotational movement of the actuator, the electromagnetic interference resulting from the passing of current through the actuator to actuate rotation, interference in the rotational movement of the actuator caused by the communication lines, and/or other factors impair the ability to simply run the communication lines across the rotational actuator to the imaging element in an suitable and effective manner. Accordingly, some specific techniques for running communication lines from a proximal portion of the rotational actuator 300 to the imaging element 301 at the distal portion of the rotational actuator are discussed below in the context of exemplary embodiments of the present disclosure.

Similar to rotational actuator 200 discussed above, the rotational actuator 300 includes a conductive pathway that is particularly suited to facilitate the application of current to the shape-memory elements of the actuator 300. As shown, the rotational actuator 300 includes an anchor 302 and an anchor 304. A pair of shape-memory elements 306 and 308 extend between and are secured to the anchors 302 and 304. Also, a bias element 310 extends between and is secured to the anchors 302 and 304. As discussed above, transitions between the twisted and un-twisted (or less twisted) orientations of the shape-memory elements 306 and 308 (caused by activating and deactivating the shape-memory elements) drive the rotational motion of the actuator 300 and, in turn, the imaging element 301 coupled to the distal portion of the actuator. In that regard, in some embodiments, the anchor 302 is configured to be fixedly secured to a flexible elongate member while the anchor 304 is able to rotate with respect to the flexible elongate member. Accordingly, with the imaging element 301 secured to the anchor 304, rotation of the anchor 304 caused by the shape-memory elements 306 and 308 of the rotational actuator 300 will also cause rotation of the imaging element 301. The imaging element 301 may be secured to the anchor 304 in any suitable manner including, without limitation, using adhesives (e.g., epoxy, glue, etc.), mechanical connections, solder, and/or combinations thereof. In that regard, in some embodiments the imaging element 301 is electrically isolated from the anchor 304 to prevent the flow of current through anchor 304, as discussed below, from affecting the function of imaging element 301.

The shape-memory elements 306 and 308 and the bias element 310 are electrically coupled to the anchors 302 and 304 in a manner that facilitates selective application of current to the shape-memory elements 306 and 308 to selectively activate and deactivate the shape-memory elements. In that regard, a proximal portion of the shape-memory element 306 is secured to a conductive inner portion 312 of the anchor 302 by connection 314. In some instances, the inner portion 312 is core wire formed of a conductive material. For example, in one embodiment the inner portion 312 is a wire having a diameter between about 0.002" (0.051 mm) and about 0.0373" (0.95 mm). In one particular embodiment, the inner portion is tungsten wire having 0.004" diameter. A distal portion of the shape-memory element 306 is secured to an extension of the anchor 314 by connection 316. Similarly, a proximal portion of the shape-memory element 308 is secured to the inner portion 312 of the anchor 302 by connection 318, while a distal portion of the shape-memory element 308 is secured to the extension of the anchor 304 by connection 320. Bias element 310, which is formed of a conductive material, has a proximal portion that is secured to a conductive outer portion 322 of the anchor 302 by connection 324 and an opposing distal portion that is secured to the anchor 304 by connection 326. A conductor 328 is secured to the inner portion 312 of the anchor 302 by connection 330, while a conductor 332 is secured to outer portion 322 of the anchor 302 by connection 334. In that regard, in some instances outer portion 322 of the anchor 302 is a hypotube having an inner diameter between about 0.003" (0.0762 mm) and about 0.038" (0.97 mm). Conductors 328 and 332 extend proximally along the length a flexible elongate member in some instances. Generally, the connections 314, 316, 318, 320, 324, 326, 330, and 334 are representative of an electrical connection. In some instances, each of the connections 314, 316, 318, 320, 324, 326, 330, and 334 is a weld and/or a mechanical connection.

An insulating layer 336 electrically insulates the inner portion 312 of the anchor 302 from the outer portion 322 of the anchor. In some instances, the insulating layer 336 is formed of polyimide. In some instances, the insulating layer 336 extends distally from the anchor 302 to the anchor 304 over the shape-memory elements 306 and 308. For example, in some embodiments the insulating layer 336 is formed as a sleeve, tube, or similar elongate structure that extends along the length of the actuator 300 over all or a majority of the length of the shape-memory elements 306 and 308. In other instances, a separate insulating structure is positioned over the shape-memory elements 306 and 308. In some instances, the insulating layer has a thickness between about 0.005" (0.127 mm) and about 0.01" (0.254 mm). In one particular embodiment, the insulating layer has a thickness of about 0.005" (0.127 mm). In some instances the insulating layer provides a structure around which one or more communication lines associated with the imaging element 301 can be wrapped or coiled in a manner that does not interfere with the rotational function of the actuator 300 and, in particular, the shape-memory elements 306 and 308.

In the illustrated embodiment, a communication line 338 is shown extending from proximal of the anchor 302 distally to the imaging element 301. A portion 340 of communication line 338 is wrapped or coiled around the shape-memory elements 306 and 308 and inside of the bias element 310. In that regard, the communication line 338 is representative of any type of communication line or connection that may be utilized with imaging element 301, including a single electrical conductor or pathway, a plurality of electrical conductors or pathways, a single optical fiber or pathway, a plurality of optical fibers or pathways, and/or combinations thereof. Accordingly, in some instances the communication line 338 is configured to extend proximally along a majority of a length of a flexible elongate member. In other instances, the communication line 338 extends to one or more components of an imaging arrangement positioned within the flexible elongate member proximal of the anchor 302. For example, in some instances the communication line 338 is coupled to multiplexer(s), optical connector(s), and/or other component(s) positioned within a distal portion of the flexible elongate member, but proximal of the anchor 302.

In some embodiments where the communication line 338 includes two or more communication lines, the plurality of communication lines are coupled together (e.g., side-by-side, twisted together, wrapped in a common housing or casing, etc.) such that the plurality of communication lines form a single structure that is wrapped or coiled around the shape-memory elements 306 and 308. For example, in the illustrated embodiment the communication line 338 consists of two communication lines 342 and 344 that are coupled to the imaging element 301. However, the communication lines 342 and 344 are coupled together (e.g., as a twisted pair, side-by-side, or other arrangement) along a majority of the length of the communication line 338. In that regard, the communication lines 342 and 344 are coupled together along the portion 340 of the communication line 338 that is wrapped or coiled around the shape-memory elements 306 and 308 (or an insulating layer when an insulating layer extends over the shape-memory elements 306 and 308). In other embodiments where the communication line 338 includes two or more communication lines, the plurality of communication lines are not coupled together but instead are each wrapped or coiled separately around the shape-memory elements 306 and 308. In some such instances, the plurality of communication lines are wrapped or coiled separately, but collective form a specific pattern or braiding arrangement.

Wrapping the communication line(s) around the shape-memory elements 306 and 308 provides stress relief. In that regard, by wrapping the communication line(s) into a spring-like or other flexible form, the communication line(s) are able to flex and rotate with the anchor 304 of the actuator 300 without undue stress on the communication line(s) or the connection(s) between the communication line(s) and the imaging element 301. Further, wrapping the communication line(s) around the shape-memory elements 306 and 308 results in a negligible opposing force during the untwisting process and negligible assisting force during the twisting process. In that regard, compared to the bias element 310 the wrapped communication line(s) provide very little opposing or assisting force. In that regard, generally speaking, the more times the communication line(s) are wrapped around the shape-memory elements 306 and 308 the smaller the contribution of the communication line(s) to the twisting and/or untwisting forces. Accordingly, in some embodiments the communication line(s) are wrapped between about 1 and about 100 times between the anchor 302 and the imaging element 301. In that regard, in some instances the communication line(s) are wrapped more than 2 times, more than 3 times, more than 4 times, more than 5 times, more than 10 times, more than 20 times, more than 30 times, more than 40 times, more than 50 times, and/or more than 100 times between the anchor 302 and the imaging element 301.

As assembled, the actuator 300 provides the communication path(s) for communicating with the imaging element 301 via communication line 338 and also provides an electrical path for selectively activating and deactivating the shape-memory elements 306 and 308. With respect to the electrical path, a current supplied along conductor 328 is passed through inner portion 312 of anchor 302 to the shape-memory elements 306 and 308. The insulating layer 336 ensures the current travels through the shape-memory elements by preventing the current from shorting through to the outer portion 322 of the anchor 302. From the shape-memory elements 306 and 308, the current passes through the anchor 304 to the distal portion of the bias element 310. In that regard, unlike anchor 302 where the inner portion 312 is electrically insulated from the outer portion 322, with anchor 304 the extension and main body are electrically coupled such that current received from the shape-memory elements 306 and 308 at the extension passes through the anchor to the distal portion of the bias element 310. However, as discussed above, the imaging element 301 is electrically decoupled from the anchor 304 in some instances. From anchor 304, the current travels along the bias element 310 to the outer portion 322 of the anchor 302 where conductor 332 is also coupled. In that regard, conductors 328 and 332 are configured to extend proximally through a flexible elongate member where they can be coupled to a voltage source for selective applying the current to the shape-memory elements.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of manufacturing an intravascular imaging device, comprising:
   providing a first anchor and a second anchor;
   fixedly securing a first shape memory element to the first anchor and the second anchor;
   fixedly securing a second shape memory element to the first anchor and the second anchor;
   rotating the second anchor relative to the first anchor such that the first and second shape memory elements are twisted together; and
   wrapping a communication line for an imaging element around the first and second shape memory elements;
   wherein the first and second shape memory elements are configured to transition between a first state and a second state such that when the first and second shape memory elements are in the first state the first and second shape memory elements are twisted together and when the first and second shape memory elements are in the second state the first and second shape memory elements are less twisted than in the first state.

2. The method of claim 1, wherein the first state is a martensite state and the second state is an austenite state.

3. The method of claim 1, further comprising fixedly securing a spring to the first anchor and the second anchor.

4. The method of claim 3, wherein the spring is positioned around the communication line such that the communication line is positioned between the first and second shape memory elements and the spring.

5. The method of claim 4, further comprising fixedly securing the first anchor to a distal portion of a flexible elongate member sized and shaped for introduction into human vasculature.

6. The method of claim 5, wherein an imaging element is coupled to the second anchor.

7. The method of claim 6, wherein the imaging element is an ultrasound transducer and the communication line comprises an electrical conductor.

8. The method of claim 6, wherein the imaging element is an optical emitter and the communication line comprises an optical fiber.

9. The method of claim 5, wherein a length between the first anchor and the second anchor is less than 5 mm after the first and second shape memory elements and the spring are secured thereto.

10. The method of claim 1, further comprising: fixedly securing a third shape memory element to the first anchor and the second anchor;
wherein rotating the second anchor relative to the first anchor causes the first, second, and third shape memory elements to be twisted together.

11. The method of claim 1, further comprising positioning an insulating member around the first and second shape memory elements, wherein wrapping the communication line for the imaging element around the first and second shape memory elements comprises wrapping the communication line around the insulating member.

12. The method of claim 1, wherein the communication line comprises a plurality of communication pathways.

13. The method of claim 12, wherein the plurality of communication pathways is selected from the group of communication pathways consisting of a plurality of electrical pathways, a plurality of optical pathways, and a combination of at least one electrical pathway and at least one optical pathway.

14. An intravascular imaging device, comprising:
a flexible elongate member;
a first anchor fixedly secured to the flexible elongate member;
a second anchor;
an imaging element coupled to the second anchor;
a spring element extending between the first and second anchors, a proximal portion of the spring element secured to the first anchor and a distal portion of the spring element secured to the second anchor;
a first shape memory element extending between the first and second anchors, a proximal portion of the first shape memory element secured to the first anchor and a distal portion of the first shape memory element secured to the second anchor;
a second shape memory element extending between the first and second anchors, a proximal portion of the second shape memory element secured to the first anchor and a distal portion of the second shape memory element secured to the second anchor; and
a communication line communicatively coupled to the imaging element, wherein at least a portion of the communication line is wrapped around the first and second shape memory elements;
wherein the first and second shape memory elements are configured to transition between a first state and a second state such that when the first and second shape memory elements are in the first state the first and second shape memory elements are in a first configuration in which the first and second shape memory elements are twisted together and when the first and second shape memory elements are in the second state the first and second shape memory elements are in a second configuration in which the first and second shape memory elements are less twisted together than in the first configuration; and
wherein the transitions of the first and second shape memory elements between the first and second states cause the second anchor to rotate about a longitudinal axis of the flexible elongate member with respect to the first anchor.

15. The rotational actuator of claim 14, wherein the first and second shape memory elements are positioned within a lumen defined by the spring element.

16. The rotational actuator of claim 14, wherein the communication line is positioned between the spring element and the first and second shape memory elements.

17. The rotational actuator of claim 14, wherein the first anchor comprises:
an inner conductive portion;
an outer conductive portion; and
an insulating portion positioned between the inner and outer conductive portions to conductively isolate the inner and outer conductive portions from one another.

18. The rotational actuator of claim 17, wherein the proximal portions of the first and second shape memory elements are conductively coupled to the inner conductive portion of the first anchor.

19. The rotational actuator of claim 18, wherein the spring is conductively coupled to the outer conductive portion of the first anchor.

20. The rotational actuator of claim 17, wherein the insulating portion extends over the first and second shape memory elements.

21. The rotational actuator of claim 20, wherein the at least a portion of the communication line is wrapped around the insulating portion.

22. The rotational actuator of claim 14, further comprising an insulating member positioned around the first and second shape memory elements, wherein the at least a portion of the communication line is wrapped around the insulating member.

23. The intravascular imaging device of claim 14, wherein the imaging element is an ultrasound imaging element.

24. The intravascular imaging device of claim 23, wherein the ultrasound imaging element is an ultrasound transducer.

25. The intravascular imaging device of claim 23, wherein the communication line is at least one electrical conductor.

26. The intravascular imaging device of claim 14, wherein the imaging element is an OCT imaging element.

27. The intravascular imaging device of claim 26, wherein the OCT imaging element is at least one fiber optic cable.

28. A method of manufacturing an intravascular imaging device, comprising:
providing a first anchor and a second anchor;
coupling an imaging element to the second anchor;
fixedly securing a first shape memory element to the first anchor and the second anchor;
fixedly securing a second shape memory element to the first anchor and the second anchor;
rotating the second anchor relative to the first anchor such that the first and second shape memory elements are twisted together; and
fixedly securing a spring to the first anchor and the second anchor;
wherein the first and second shape memory elements are configured to transition between a first state and a second state such that when the first and second shape memory elements are in the first state the first and second shape memory elements are twisted together and when the first and second shape memory elements are in the second state the first and second shape memory elements are less twisted than in the first state.

29. A rotational actuator, comprising:
a first anchor;
a second anchor;
at least one shape memory element extending between the first and second anchors, a proximal portion of the at least one shape memory element secured to the first anchor and a distal portion of the at least one shape memory element secured to the second anchor
wherein the at least one shape memory element is configured to transition between a first state and a second state such that when the at least one shape memory element is in the first state the at least one shape memory element is in a first configuration in which the at least one shape memory element is twisted and when the at least one shape memory element is in the second state the at least one shape memory element is in a second configuration in which the at least one shape memory element is less twisted than in the first configuration; and
wherein the transitions of the at least one shape memory element between the first and second states cause the second anchor to rotate about a longitudinal axis with respect to the first anchor.

* * * * *